United States Patent [19]
LeBlanc

[11] Patent Number: 5,755,573
[45] Date of Patent: May 26, 1998

[54] DENTAL POST EXTRACTOR

[76] Inventor: Edward H. LeBlanc, 6098 Fernwood Rd., Magnolia, Miss. 39652

[21] Appl. No.: 713,663

[22] Filed: Sep. 13, 1996

[51] Int. Cl.⁶ .............................. A61C 3/14; A61C 3/16; A61C 3/00
[52] U.S. Cl. ........................ 433/159; 433/161; 433/153
[58] Field of Search ........................ 433/149, 153, 433/154, 155, 157, 158, 159, 161

[56] References Cited

U.S. PATENT DOCUMENTS

| | | |
|---|---|---|
| 812,976 | 2/1906 | Carpenter . |
| 936,732 | 10/1909 | Manning . |
| 1,021,893 | 4/1912 | Ross . |
| 1,035,744 | 8/1912 | Ross ........................................ 433/154 |
| 1,072,517 | 9/1913 | Skinner . |
| 1,072,518 | 9/1913 | Skinner . |
| 1,072,519 | 9/1913 | Skinner . |
| 1,072,520 | 9/1913 | Skinner . |
| 1,072,521 | 9/1913 | Skinner . |
| 1,105,755 | 8/1914 | Chamberlin et al. . |
| 1,158,872 | 11/1915 | Trabold et al. . |
| 2,027,470 | 1/1936 | Caruso . |
| 2,497,229 | 2/1950 | Moller ........................................ 433/154 |

*Primary Examiner*—Nicholas D. Lucchesi
*Attorney, Agent, or Firm*—Phelps Dunbar

[57] ABSTRACT

A dental post extractor which includes a main body having a fixed jaw against which a second movable jaw is urged to grasp a dental post. The main body also includes a fixed handle against which a second movable handle may be urged, creating lateral movement in an elongated plate that extends through the main body. Lateral movement in the elongated plate causes downward force to be exerted on the tooth containing the dental post, resulting in the removal of the post.

4 Claims, 1 Drawing Sheet

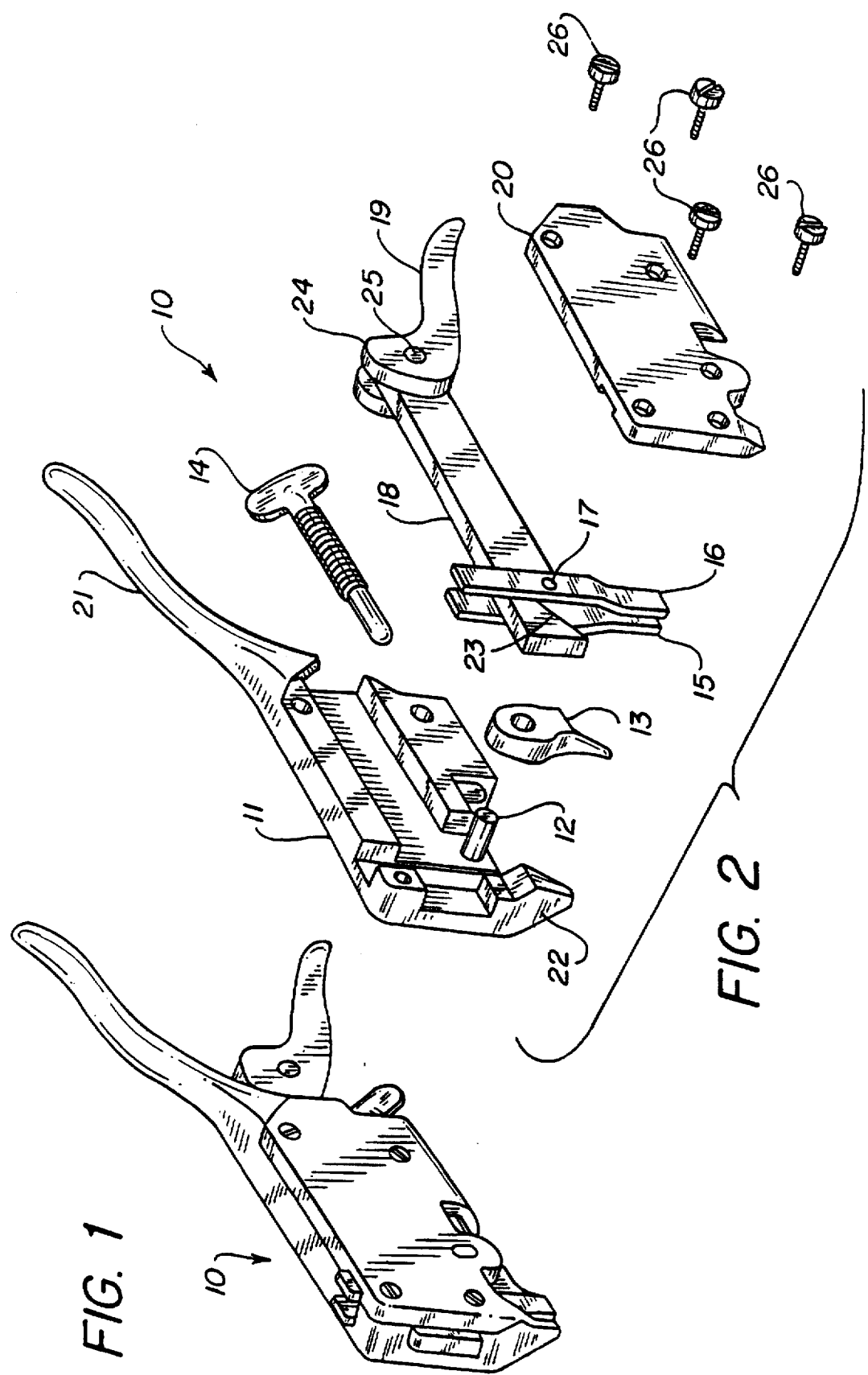

DENTAL POST EXTRACTOR

BACKGROUND OF THE INVENTION

This invention relates in general to improvements in dental equipment used to extract posts previously inserted into teeth. This invention particularly relates to dental post extractors which have a minimum of moving parts, are simple and easy to disassemble and reassemble, and which offer means to quickly and easily sense and vary the pressure applied to facilitate removal of dental posts.

It is a practice in the dental profession to drill a hole in the base of a tooth for root canal and other reasons and then to cement a metal post in the hole. The post extends above the tooth and becomes support for a crown or bridgework. It sometimes becomes necessary to extract the post for various reasons, such as tooth decay around the post, to insert a larger post, to facilitate bridgework and other problems. Current methods of extracting a post include: the use of an instrument such as a hemostat to grip the post in order to use force of hand to manipulate the post out of the tooth, or cutting the post flush with the surface of the tooth and drilling out the remaining portion of the post. This is time consuming and is uncomfortable for the patient.

Those dental post extractors currently on the market suffer from limitations that arise out of changes that the practice of dentistry has undergone over the past 10 years. Newly emerging concerns regarding infectious diseases have caused a complete reevaluation of the dental practice. Protection of the patient and of the dental practitioner requires reevaluation of all techniques employed by the practitioner. Particular emphasis must be placed upon the ability to thoroughly clean any dental instrument which is to be reused on another patient. Existing dental post extractors are not well suited to this need. They often cannot be disassembled, making thorough cleaning difficult if not impossible. Those that can be disassembled often are not easily reassembled, which discourages disassembly and cleaning of the instrument.

Existing dental post extractors also do not provide the practitioner with a means to sense and easily adjust the force being applied to remove the dental post. Many involve the use of threaded devices to apply downward force on the tooth or surrounding teeth. These threaded devices limit the ability of the practitioner to feel or sense the amount of force being applied. They also can be difficult to operate, as the size of the head of the threaded device can limit the lever arm available for development of the needed torque.

SUMMARY OF THE INVENTION

With the use of the disclosed invention, the dentist can quickly and easily remove the post and not harm the tooth. The extractor is set on the post and locked with the use of a thumb screw and the post is extracted by squeezing a handle. The extractor is comprised of only a few moving parts, and is easily disassembled and reassembled, facilitating complete and thorough cleaning of the extractor. The disclosed invention does not utilize threaded means for applying downward pressure on the tooth. Instead, such pressure is generated by squeezing a handle between the fingers and palm of the hand, and is transferred to the tooth by the use of two cam-like surfaces, one near each end of a slidable member housed within the main body of the invention.

The advantages of the disclosed dental post extractor are substantial. The use of a minimum of moving parts that can be easily disassembled enables the dental assistant to thoroughly clean the device between uses. No areas of the extractor are difficult to reach or view once disassembled. Furthermore, the disclosed extractor gives the practitioner the ability to feel the extent to which pressure is applied to the tooth, and to immediately alter that pressure if needed. Threaded means to apply pressure to the tooth do not enjoy such benefits.

It is an object of this invention to provide a dental post extractor which is easy to disassemble and reassemble.

It is an object of this invention to provide a dental post extractor which is easy to thoroughly clean.

It is an object of this invention to provide a dental post extractor in which it is easy for the practitioner to feel the downward force applied to the tooth.

These and other objects of the invention will be more apparent to those skilled in the art from the following detailed description of the invention.

BRIEF DESCRIPTION OF THE DRAWINGS

Reference will be made to the drawings wherein like parts are designated by like numerals and wherein:

FIG. 1 is a perspective view of the dental post extractor; and

FIG. 2 is an exploded view of the dental post extractor.

DETAILED DESCRIPTION OF THE PREFERRED EMBODIMENT

FIG. 1 illustrates an assembled extractor 10 ready to extract a post from a tooth. FIG. 2 is an exploded view of the extractor 10 in which the various parts of the extractor are shown. The main body 11 has a fixed handle 21 at one end and a fixed jaw 22 at the opposite end and two grooves for acceptance of internal sliding parts 15, 16 and 18, described in detail later. Pin 12 is fixed in body 11 and extends so that swivel jaw 13 can be mounted on it and can rotate or swivel about pin 12. The swivel or rotation of swivel jaw 13 is controlled by the thumb screw 14. It can be seen that by turning thumb screw 14 pressure will be applied on swivel jaw 13 and cause swivel jaw 13 to move toward fixed jaw 22. In this manner the fixed jaw 22 and swivel jaw 13 can work in concert to grasp and securely hold a dental post. Lifters 15 and 16 are assembled into a unit by lifter pin 17. The lifter unit comprised of lifters 15 and 16 and pin 17 slides in a groove in the main body 11. The ends of lifters 15 and 16 proximate the swivel jaw 13 and fixed jaw 22 rest on the tooth containing the dental post. Elongated member 18 slides in a groove in the main body and in between lifters 15 and 16. The end of elongated member 18 which extends between lifters 15 and 16 contains tapered surface 23. It can be seen that by retracting elongated member 18 the angle on tapered surface 23 will exert pressure on lifter pin 17 and thereby cause the main body 11 to rise. When the swivel jaw 13 and fixed jaw 22 are locked on a dental post, the post will rise as the main body 11 rises due to the opposite pressure exerted on the tooth. The retraction of elongated member 18 is caused by cam surface 24 on movable handle 19, when movable handle 19 is urged toward fixed handle 21. The cam surface 24 on movable handle 19 rotates about handle pin 25 that extends through elongated member 18. The cam surface 24 on movable handle 19 exerts pressure on both main body 11 and closure plate 20 when the movable handle 19 is urged toward the fixed handle 21, causing the elongated member 18 to retract. Retraction of elongated member 18 results in downward force being applied to lifter pin 17 and lifters 15 and 16. By means of screws 26 or other easily removable fasteners, closure plate 20 is locked against the main body 11 and the extractor 10 is then in an assembled state. The extractor 10 may be easy assembled and disassembled numerous times, facilitating cleaning of the instrument between uses.

In use the fixed jaw 22 and swivel jaw 13 of extractor 10 are placed over a dental post to be removed. By advancing thumb screw 14, swivel jaw 13 is urged toward fixed jaw 22, until the dental post is firmly locked between swivel jaw 13 and fixed jaw 22. The practitioner then carefully applies pressure to movable handle 19 and fixed handle 21, urging them together. As explained above, this causes elongated member 18 to retract, which exerts downward pressure on lifter pin 17 and lifters 15 and 16, which in turn exert downward pressure on the tooth containing the dental post. The dental practitioner exerts the pressure required to make the dental post leave its seat in the tooth. After use the dental post extractor is disassembled by simply retracting screws 26 and thumb screw 14. All parts of the extractor may then be thoroughly cleaned and easily reassembled, ready to be used again.

What I claim is:

1. An instrument for extracting dental posts from teeth, comprising;
    a main body containing a fixed jaw and removable closure plate,
    a handle fixably attached to said main body,
    a movable jaw mounted to said main body,
    a threaded screw attached to said main body, the leading end of which contacts said movable jaw and urges said movable jaw toward said main body when said threaded screw is advanced, whereby a dental post may be locked between said movable jaw and said fixed jaw,
    one or more lifter plates slidably contained within said main body for contacting a tooth containing a dental post,
    an elongated plate slidably contained within said main body,
    a movable handle mounted to one end of said elongated plate,
    one or more cam surfaces proximate the end of said movable handle mounted to said elongated plate, said one or more cam surfaces contacting said main body and configured whereby compression of said movable handle toward said fixed handle causes said elongated plate to retract, and
    means for contacting said elongated plate with said one or more lifter plates, whereby said one or more lifter plates are urged downward as said elongated plate retracts.

2. A device as in claim 1 wherein said means for contacting said elongated plate with said one or more lifter plates comprises a contact surface on said elongated plate that gradually tapers so as to alter the width of said elongated plate, said contact surface on said elongated plate being in contact with said one or more lifter plates, whereby said one or more lifter plates are urged downward as said elongated plate is retracted.

3. A device as in claim 1 wherein the direction of movement of said elongated plate is perpendicular to the direction of movement of said one or more lifter plates.

4. A device as in claim 1 herein said movable jaw, said elongated plate, said one or more lifter plates, said threaded screw, and said movable handle all may be removed from said main body upon removal of said removable closure plate.

* * * * *